(12) United States Patent
Wang et al.

(10) Patent No.: US 8,119,816 B2
(45) Date of Patent: Feb. 21, 2012

(54) MEROCYANINE DYE AND USE THEREOF

(75) Inventors: Fu-Shing Wang, Taoyuan (TW); Kuang-Mei Hsu, Taoyuan (TW)

(73) Assignee: Taiwan Fluoro Technology Co., Ltd., Taichung (TW)

( * ) Notice: Subject to any disclaimer, the term of this patent is extended or adjusted under 35 U.S.C. 154(b) by 870 days.

(21) Appl. No.: 11/549,563

(22) Filed: Oct. 13, 2006

(65) Prior Publication Data

US 2007/0085074 A1 Apr. 19, 2007

Related U.S. Application Data

(60) Provisional application No. 60/726,378, filed on Oct. 13, 2005.

(51) Int. Cl.
*C07D 209/56* (2006.01)
*C07D 411/02* (2006.01)
*C07D 487/00* (2006.01)
*C07D 211/00* (2006.01)
*C07D 215/12* (2006.01)

(52) U.S. Cl. .......................... 548/427; 546/15; 546/176

(58) Field of Classification Search .................. 548/427, 548/468, 364.7
See application file for complete search history.

(56) References Cited

U.S. PATENT DOCUMENTS

| | | | | |
|---|---|---|---|---|
| 3,840,375 | A * | 10/1974 | Sauter | 430/522 |
| 4,757,046 | A * | 7/1988 | Byers et al. | 503/227 |
| 6,596,364 | B2 | 7/2003 | Shimizu et al. | |
| 6,835,725 | B2 * | 12/2004 | Berneth et al. | 514/183 |
| 2002/0009669 | A1 | 1/2002 | Morishima et al. | |
| 2002/0064782 | A1 | 5/2002 | Shinoki et al. | |
| 2003/0003396 | A1 | 1/2003 | Berneth et al. | |

FOREIGN PATENT DOCUMENTS

| | | |
|---|---|---|
| DE | 10109243 | 9/2002 |
| EP | 1253148 | 10/2002 |
| EP | 1652892 | 5/2006 |
| WO | WO 0280161 | * 3/2002 |
| WO | 2006038464 | 4/2006 |

OTHER PUBLICATIONS

Umehara et al. STN Accession No. 1984:165332; Document No. 100:165332. Abstract of Nippon Kagaku Kaishi, 1984, 192-9.*

* cited by examiner

*Primary Examiner* — Nizal Chandrakumar

(57) ABSTRACT

The present invention provides a blue laser light-absorbent substance, which is suitably used in organic photo conductor, laser optical data carrier or organic light-emitting diodes. The blue laser light-absorbent substance includes a merocyanine compound of the general formula (1)

wherein n is an integer of from 0 to 3; $R_1$ is unsubstituted or phenyl-, halogen-, ester-, siliy-substituted linear or branched alkyl group having 1 to 6 carbon atoms; $R_2$ is unsubstituted or substituted phenyl, benzyl or naphthyl; N and $R_1R_2$ together represent aromatic-fused N-containing heterocyclic group ($NR_1R_2$); $Y_1$ is unsubstituted or substituted alkoxy group having 1 to 8 carbon atoms; $Y_2$ is cyano, nitro, halogen or carboxylate; or O and $Y_1Y_2$ together represent epoxy or N-containing heterocyclic hydrocarbonyl ketone ($OY_1Y_2$).

4 Claims, 6 Drawing Sheets

| No. | Structure | $\lambda_{max}$(in MeOH) |
|---|---|---|
| M2600 | 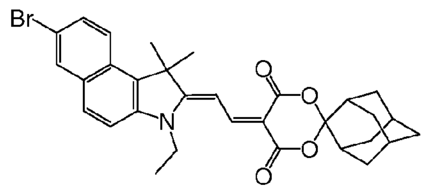 | 470 nm |
| M2601 | 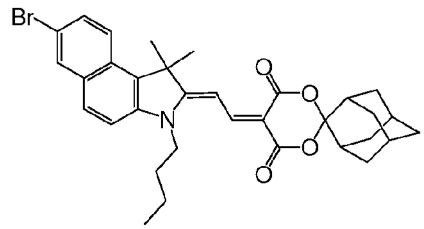 | 471 nm |
| M2602 | 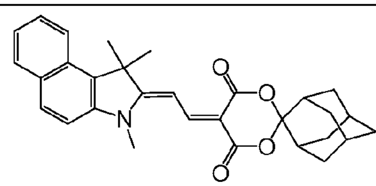 | 460 nm |
| M2603 | 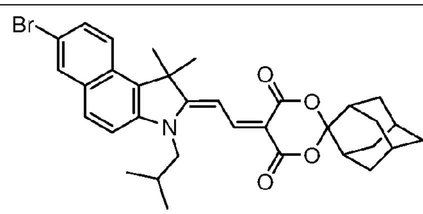 | 471 nm |
| M2604 | 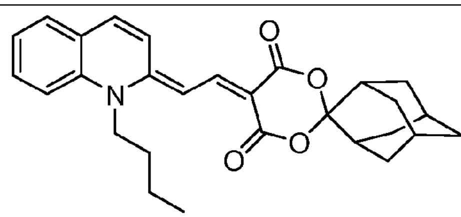 | 480 nm |
| M2605 | 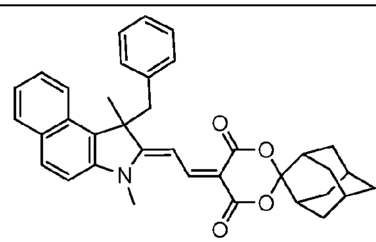 | 465 nm |
| M2700 | 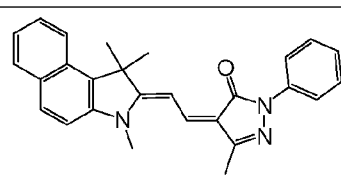 | 491 nm |

Fig.1(A)

| No. | Structure | λ$_{max}$(in MeOH) |
|---|---|---|
| M2701 | 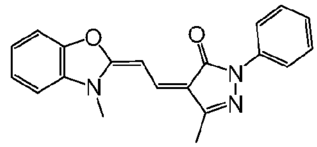 | 449 nm |
| M2702 | 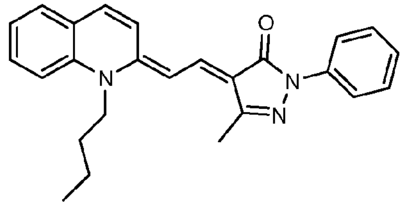 | 512 nm |
| M2703 | 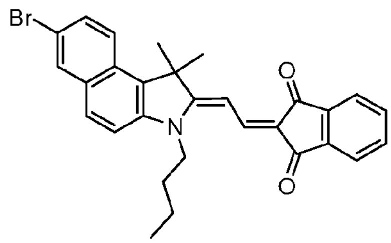 | 515 nm |
| M2704 | 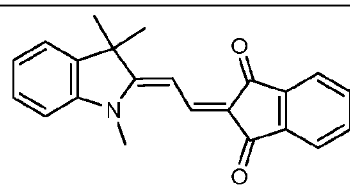 | 493 nm |
| M2800 | 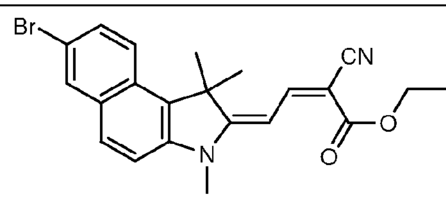 | 454 nm |
| M2801 | 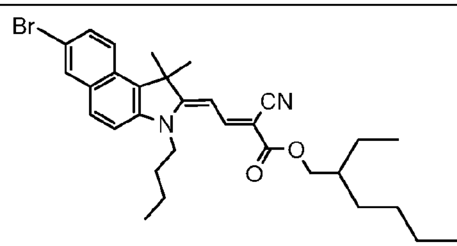 | 454 nm |
| M2802 | 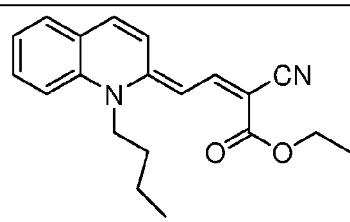 | 469 nm |

MEROCYANINE DYE AND USE THEREOF

FIELD OF THE INVENTION

The present invention relates to a merocyanine dye, and more particularly to a merocyanine dye having an absorption peak in the spectral wavelength range of a blue laser. The present invention also relates to the uses of the merocyanine dye in organic photo conductors, laser optical data carriers or organic light-emitting diodes.

BACKGROUND OF THE INVENTION

Blue laser light has very widespread applications. For example, the blue laser light may be applicable to high-density optical storage or even medical science. Conventionally, the high-density optical data stores are operated with red diodes at the wavelength of about 650 nm. Through the use of shorter-wavelength blue laser radiation (about 405 nm), the next generation of optical data stores, e.g. DVDs, are currently introduced onto the market to be written or read by means of a blue laser light in a high-density manner. Generally, the DVDs applied in the blue laser technology are classified into two types, for example blu-ray discs and advanced optical discs (AODs).

According to the blue laser technology, the light-absorbent substances used in the optical discs are very important for adsorbing blue laser light. Generally, the light-absorbent substances include organic dyes and inorganic phase-changeable materials. The organic dyes displaying an intense absorption in the wavelength range of 390 to 490 nm (e.g. 405 nm) can be used for adsorbing the blue laser light. Examples of the organic dyes include cyanines, porphyrins, polyenes, azo compounds, dicyanovinylphenyl compounds, etc.

To achieve excellent optical properties, the dyes should have a high molar extinction coefficient at the blue light absorption wavelength. Moreover, photosensitivity, solubility, light fastness and writing power are also important for selecting suitable dyes.

Therefore, there is a continuous need of providing better blue laser light-absorbent substances, which can satisfy the abovementioned requirement profile particularly well.

SUMMARY OF THE INVENTION

The present invention provides a blue laser light-absorbent substance, which is suitably used in organic photo conductors, laser optical data carriers or organic light-emitting diodes. The blue laser light-absorbent substance includes a merocyanine compound of the general formula (1)

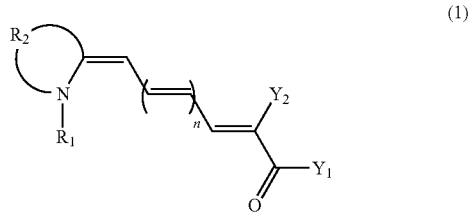

(1)

wherein n is an integer of from 0 to 3; $R_1$ is unsubstituted or phenyl-, halogen-, ester-, siliy-substituted linear or branched alkyl group having 1 to 6 carbon atoms; $R_2$ is unsubstituted or substituted phenyl, benzyl or naphthyl; N and $R_1R_2$ together represent aromatic-fused N-containing heterocyclic group ($NR_1R_2$); $Y_1$ is unsubstituted or substituted alkoxy group having 1 to 8 carbon atoms; $Y_2$ is cyano, nitro, halogen or carboxylate; or O and $Y_1Y_2$ together represent epoxy or N-containing heterocyclic hydrocarbonyl ketone ($OY_1Y_2$).

Preference is given to using a merocyanine compound having an absorption peak in the spectral range of from 390 to 490 nm.

In the left side of the formula (1), the group $NR_1R_2$ is selected from oxazole, quinoline or indole aromatic group, wherein the indole aromatic group is optionally bromide-substituted and the 5-membered azacyclic ring thereof is optionally benzyl-substituted.

In the right side of the formula (1), the group $OY_1Y_2$ is preferably selected from cyanocarboxylate, pyrazolone, indanedione or dioxanedione group, wherein the dioxanedione group is optionally adamantyl-substituted, and the pyrazolone group is optionally phenyl-substituted.

BRIEF DESCRIPTION OF THE DRAWINGS

The above contents of the present invention will become more readily apparent to those ordinarily skilled in the art after reviewing the following detailed description and accompanying drawings, in which:

FIGS. 1(A) and 1(B) illustrate a series of exemplary merocyanine compounds of the present invention;

DETAILED DESCRIPTION OF THE PREFERRED EMBODIMENT

The present invention provides a merocyanine compound adapted to be used as a dye component of an optical disc. Moreover, by replacing one or more substituents, this dye component has improved properties such as photosensitivity, solubility, light fastness and the optical disc containing this dye component may be written in a reduced writing power.

The merocyanine compound of the present invention has the general formula (1)

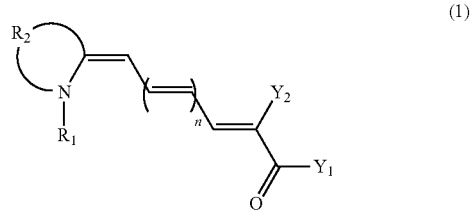

(1)

wherein n is an integer of from 0 to 3; $R_1$ is unsubstituted or phenyl-, halogen-, ester-, siliy-substituted linear or branched alkyl group having 1 to 6 carbon atoms; $R_2$ is unsubstituted or substituted phenyl, benzyl or naphthyl; N and $R_1R_2$ together represent aromatic-fused N-containing heterocyclic group ($NR_1R_2$); $Y_1$ is unsubstituted or substituted alkoxy group having 1 to 8 carbon atoms; $Y_2$ is cyano, nitro, halogen or carboxylate; or O and $Y_1Y_2$ together represent epoxy or N-containing heterocyclic hydrocarbonyl ketone ($OY_1Y_2$).

Figure 1B:
Figure 1B:
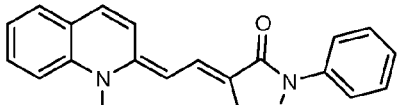
Figure 1B:
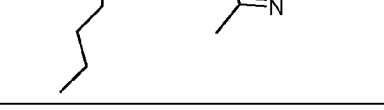
Figure 1B:
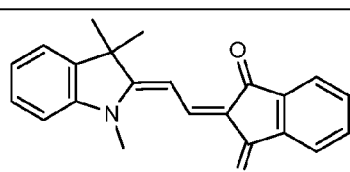
Figure 1B:
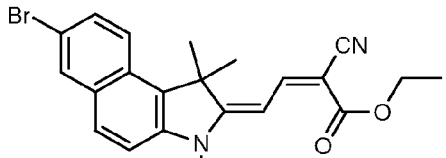
Figure 1B:
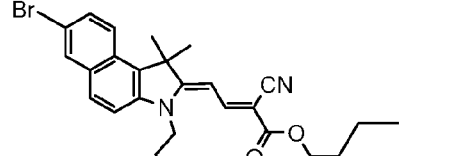
Figure 1B:
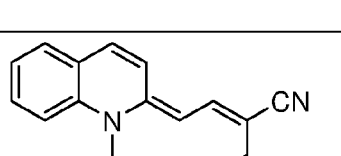

In FIGS. 1(A) and 1(B), a series of exemplary merocyanine compounds which are suitable as dye components of the optical discs are shown in Table 1.

As shown in Table 1, each of the merocyanine compounds has a conjugated double bond in the backbone. Depending on the desired performance and the production process, the merocyanine compounds of the present invention may have more conjugated double bonds.

In the left side of the formula (1), the group $NR_1R_2$ is selected from oxazole, quinoline or indole aromatic group. The indole aromatic groups of the merocyanine compounds M2600, M2601, M2603, M2703, M2800 and M2801 are bromide-substituted. The 5-membered azacyclic ring of the merocyanine compound M2605 is benzyl-substituted. The bromide substituent may increase the sensitivity of the optical disc to the laser light. The benzyl substituent may largely reduce the thermal decomposition temperature of the merocyanine compound, which is considerable when the writing power is measured at a high revolving speed.

In the right side of the formula (1), the group $OY_1Y_2$ is preferably selected from cyanocarboxylate, pyrazolone, indanedione or dioxanedione group. The dioxanedione groups of the merocyanine compounds M2600, M2601, M2602, M2603, M2604 and M2605 are adamantyl-substituted. The pyrazolone groups of the merocyanine compounds M2700, M2701 and M2702 are phenyl-substituted. The adamantly substituent may increase the weather resistance, and the phenyl substituent may increase the light fastness.

The absorption peaks ($\lambda_{max}$) of the merocyanine compounds in methanol are also shown in FIGS. 1(A) and 1(B). These absorption peaks ($\lambda_{max}$) lie within the spectral range of blue laser light, and thus these merocyanine compounds can be used in organic photo conductor, laser optical data carrier or organic light-emitting diodes.

Hereinafter, the uses of the merocyanine compounds of the present invention as light-absorbent substances in blue laser DVDs are illustrated. The following examples are included for illustrative purposes and do not limit the scope of the present invention.

Example 1

Preparation Procedure 1

13.3 g of 2-methylbenzo[d]oxazole and 21.3 g of methyl iodide were dissolved in 13.3 ml of acetonitrile, and heated to reflux for 8 hours to form a reaction solution. After the reaction solution is cooled to 50° C., 26.6 ml of acetone is added into the reaction solution to precipitate the crude products. After cooling to room temperature, the precipitates were filtered and washed with 13.3 ml of acetone. The precipitates were dried in oven at 80° C. to give 21.3 g of white crystalline powder as an intermediate compound.

Preparation Procedure 2

13.8 g of the white crystalline powder prepared in preparation procedure 1, 19.6 g of N,N-diphenylformamidine, and 4.1 g of sodium acetate were dissolved in 41.4 ml of ethanol, and heated to reflux for 2 hours. After cooling to room temperature, the precipitates were filtered and washed with 13.8 ml of methanol. The precipitates were dried in oven at 80° C., and then further purified by column with ethyl acetate, to give 9.2 g of yellow crystalline powder as an intermediate compound.

Preparation Procedure 3

Figure 2:
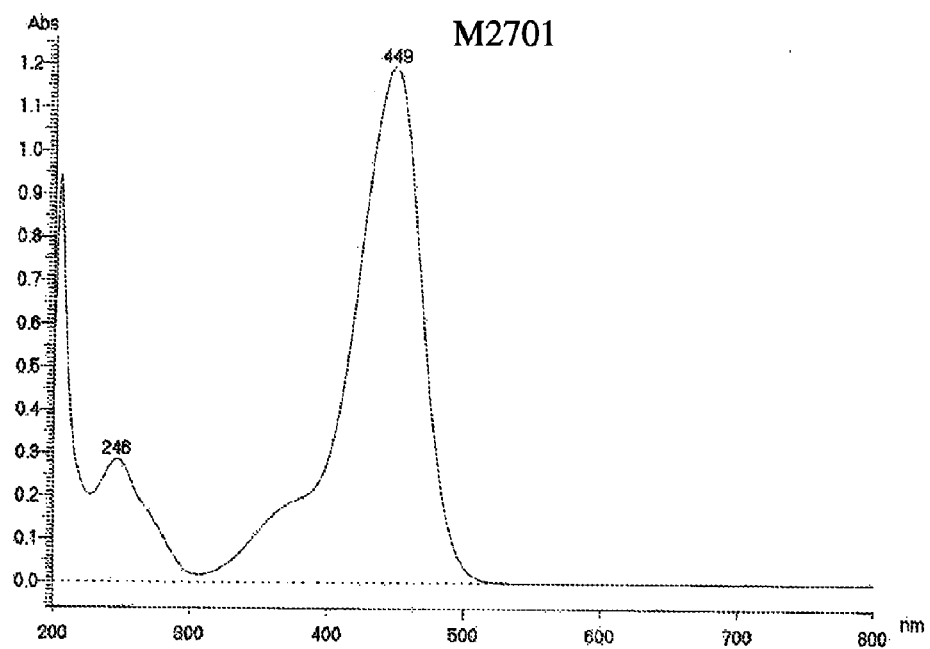
FIG. 2 is a UV-Vis absorption spectrum of the merocyanine compound M2701.

3.8 g of the yellow crystalline powder prepared in preparation procedure 2 and 1.7 g of 3-methyl-1-phenyl-2-pyrazole-5-one were dissolved in 11.4 ml of DMF at room temperature to form a reaction solution. Then, 2 g of triethylamine was added dropwise into the reaction solution, and stirred at room temperature for 5 hours. 11.4 ml of methanol was added into the reaction solution. The precipitates were filtered and washed with 5.7 ml of methanol, and dried in oven at 80° C. to give 2.4 g of yellow powder as the final product, i.e. the merocyanine compound M2701 of the formula (2). As shown in the absorption spectrum of FIG. 2, the absorption peak ($\lambda_{max}$) of this merocyanine compound M2701 in methanol is 449 nm.

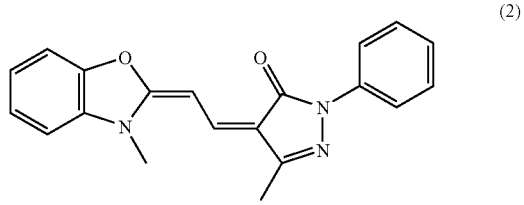

(2)

The merocyanine compound of formula (2) was dissolved in 2,2,3,3-tetrafluoropropanol or other suitable solvent such as trifluoroethanol or octafluoropentanol. The resulting solution was filtered through the Teflon filter having a pore width of 0.2 micrometer and was applied to a polycarbonate disc by the spin-coating process. The dimensions of the disc corresponded to those customarily used for DVD. The disc with the merocyanine dye layer was tested by means of a writing test apparatus comprising a blue laser diode. The light reflected from the reflection layer of the disc was measured and the reflectivity is 30%. At a writing power of 6.5 mW, the carrier-to-noise ratio (CNR) of a reproduced signal at 2T (i.e. 2TCNR) is 35. The results show that the merocyanine compound M2701 satisfies the requirement profile as dye component of optical disc particularly well.

Example 2

Preparation Procedure 4

Follow the preparation procedure 1, except that 2-methylbenzo[d]oxazole used as a reactant in the preparation procedure 1 is replaced by 7-bromo-1,1,2-trimethyl-1H-benzo[e]indole and methyl iodide used as another reactant in the preparation procedure 1 is replaced by butyl iodide. The reactant, 7-bromo-1,1,2-trimethyl-1H-benzo[e]indole and another reactant, butyl iodide were dissolved in acetonitrile, and heated to reflux sufficiently to form a reaction solution. After the reaction solution is cooled to 50° C., acetone is added into the reaction solution to precipitate the crude products. After cooling to room temperature, the precipitates were filtered and washed with acetone. The precipitates were dried in oven at 80° C. to give white crystalline powder as an intermediate compound.

Preparation Procedure 5

Follow the preparation procedure 2, except that the white crystalline powder produced as the intermediate compound in the preparation procedure 1 is replaced by the white crystalline powder produced as the intermediate compound in the preparation procedure 4. The reactant, the white crystalline powder prepared in the preparation procedure 4, another reactant, N,N-diphenylformamidine, and the other reactant, sodium acetate were dissolved in ethanol, and heated to reflux sufficiently. After cooling to room temperature, the precipitates were filtered and washed with methanol. The precipitates were dried in oven at 80° C., and then further purified by column with ethyl acetate, to give yellow crystalline powder as an intermediate compound.

Preparation Procedure 6

Figure 3:
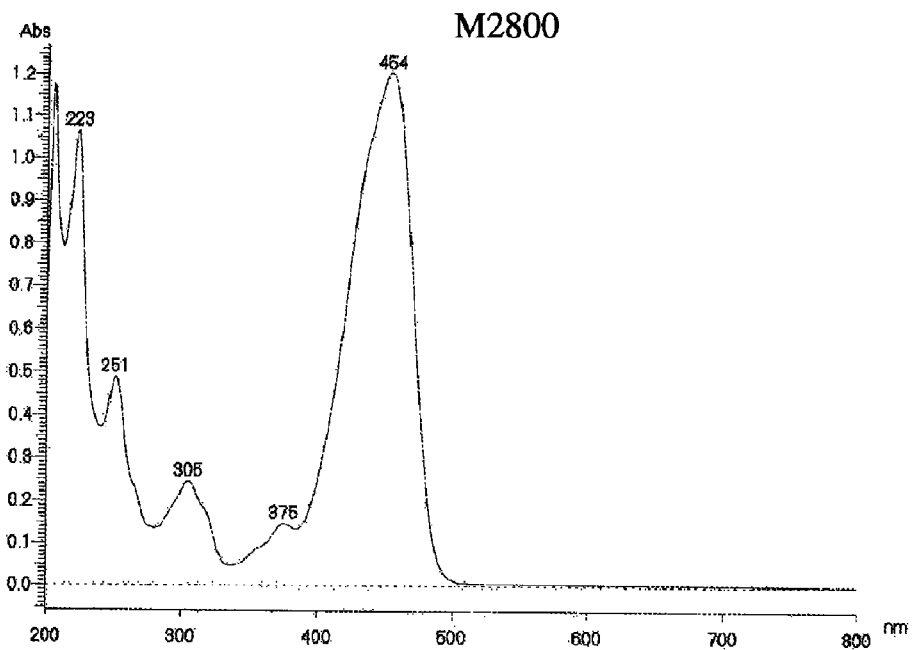
FIG. 3 is a UV-Vis absorption spectrum of the merocyanine compound M2800.

Follow the preparation procedure 3, except that the yellow crystalline powder produced as the intermediate compound in the preparation procedure 2 is replaced by the yellow crystalline powder produced as the intermediate compound in the preparation procedure 5 and the reactant, 3-methyl-1-phenyl-2-pyrazole-5-one, is replaced by ethyl-2-cyanoacetate. The reactant, the yellow crystalline powder prepared in preparation procedure 5 and another reactant, ethyl-2-cyanoacetate were dissolved in DMF at room temperature to form a reaction solution. Then, the other reactant, triethylamine was added dropwise into the reaction solution, and stirred at room temperature sufficiently. Then, methanol was added into the reaction solution. The precipitates were filtered and washed with methanol, and dried in oven at 80° C. to give yellow powder as the final product, i.e. the merocyanine compound M2800 of the formula (3). As shown in the absorption spectrum of FIG. 3, the absorption peak ($\lambda_{max}$) of this merocyanine compound M2800 in methanol is 454 nm.

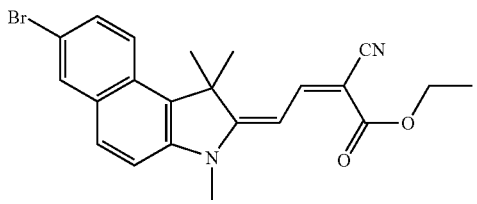

(3)

The merocyanine compound of formula (3) was dissolved in 2,2,3,3-tetrafluoropropanol. The resulting solution was filtered through the Teflon filter having a pore width of 0.2 micrometer and was applied to a polycarbonate disc by the spin-coating process. The disc with the merocyanine dye layer was tested by means of a writing test apparatus comprising a blue laser diode. The results show that the reflectivity, the writing power, the 2TCNR value of the reproduced signal satisfy the requirement profile as dye component of optical disc particularly well.

Example 3

Preparation Procedure 7

Follow the preparation procedure 1, except that 2-methylbenzo[d]oxazole used as a reactant is replaced by 1,1,2-trimethyl-1H-benzo[e]indole. The reactant, 1,1,2-trimethyl-1H-benzo[e]indole and another reactant, methyl iodide were dissolved in acetonitrile, and heated to reflux sufficiently to form a reaction solution. After the reaction solution is cooled to 50° C., acetone is added into the reaction solution to precipitate the crude products. After cooling to room temperature, the precipitates were filtered and washed with acetone, and dried in oven at 80° C. to give white crystalline powder as an intermediate compound.

Preparation Procedure 8

Follow the preparation procedure 2, except that the white crystalline powder produced as the intermediate compound in the preparation procedure 1 is replaced by the white crystalline powder produced as the intermediate compound in the preparation procedure 7. The reactant, the white crystalline powder prepared in preparation procedure 7, another reactant, N,N-diphenylformamidine, and the other reactant, sodium acetate were dissolved in ethanol, and heated to reflux sufficiently. After cooling to room temperature, the precipitates were filtered and washed with methanol. The precipitates were dried in oven at 80° C., and then further purified by column with ethyl acetate to give yellow crystalline powder as an intermediate compound.

Preparation Procedure 9

Figure 4:
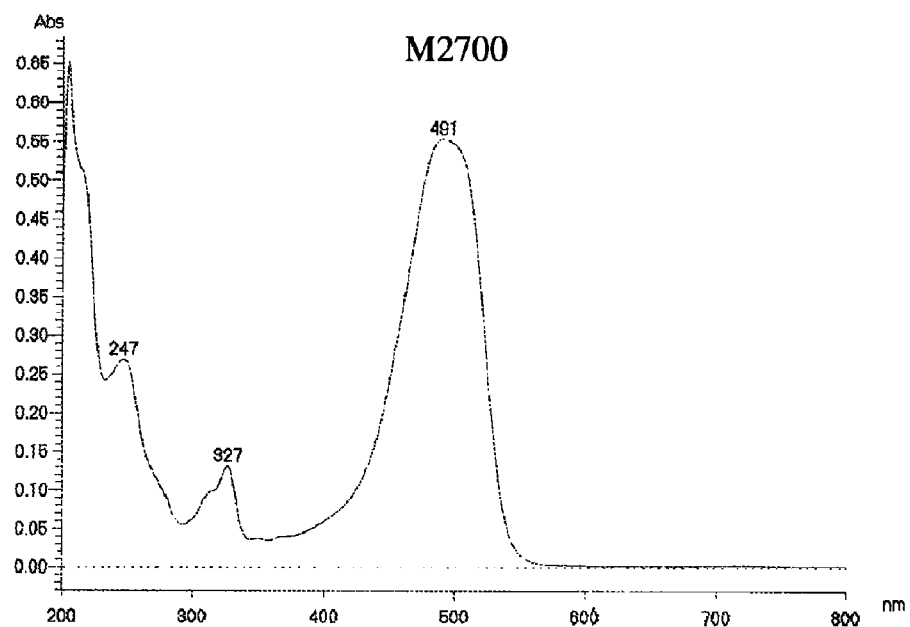
FIG. 4 is a UV-Vis absorption spectrum of the merocyanine compound M2700.

Follow the preparation procedure 3, except that the yellow crystalline powder produced as the intermediate compound in the preparation procedure 2 is replaced by the yellow crystalline powder produced as the intermediate compound in the preparation procedure 8. The reactant, the yellow crystalline powder prepared in the preparation procedure 8 and another reactant, 3-methyl-1-phenyl-2-pyrazole-5-one were dissolved in DMF at room temperature to form a reaction solution. Then, the other reactant, triethylamine was added dropwise into the reaction solution, and stirred at room temperature sufficiently. Methanol was added into the reaction solution. The precipitates were filtered and washed with methanol, and dried in oven at 80° C. to give yellow powder as the final product, i.e. the merocyanine compound M2700 of the formula (4). As shown in the absorption spectrum of FIG. 4, the absorption peak ($\lambda_{max}$) of this merocyanine compound M2700 in methanol is 491 nm.

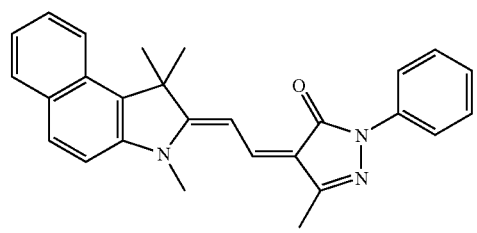

(4)

The merocyanine compound of formula (4) was dissolved in 2,2,3,3-tetrafluoropropanol. The resulting solution was filtered through the Teflon filter having a pore width of 0.2 micrometer and was applied to a polycarbonate disc by the spin-coating process. The disc with the merocyanine dye layer was tested by means of a writing test apparatus comprising a blue laser diode. The results show that the reflectivity, the writing power, the 2TCNR value of the reproduced signal satisfy the requirement profile as dye component of optical disc particularly well.

Example 4

Preparation Procedure 10

10.4 g of malonic acid and 16.5 g of adamantanone were dissolved in 16.5 ml of acetic anhydride, and then 0.2 ml of sulfuric acid was added dropwise into the reaction solution. After stirring at room temperature for 8 hours, 200 ml of water and 200 ml of hexane were poured into the reaction solution, and stirred at room temperature for 1 hour. The precipitates were filtered and washed with 100 ml of water and 100 ml of hexane, and dried in oven at 80° C. to give 20.2 g of white crystalline powder as an intermediate compound.

Preparation Procedure 11

Figure 5:
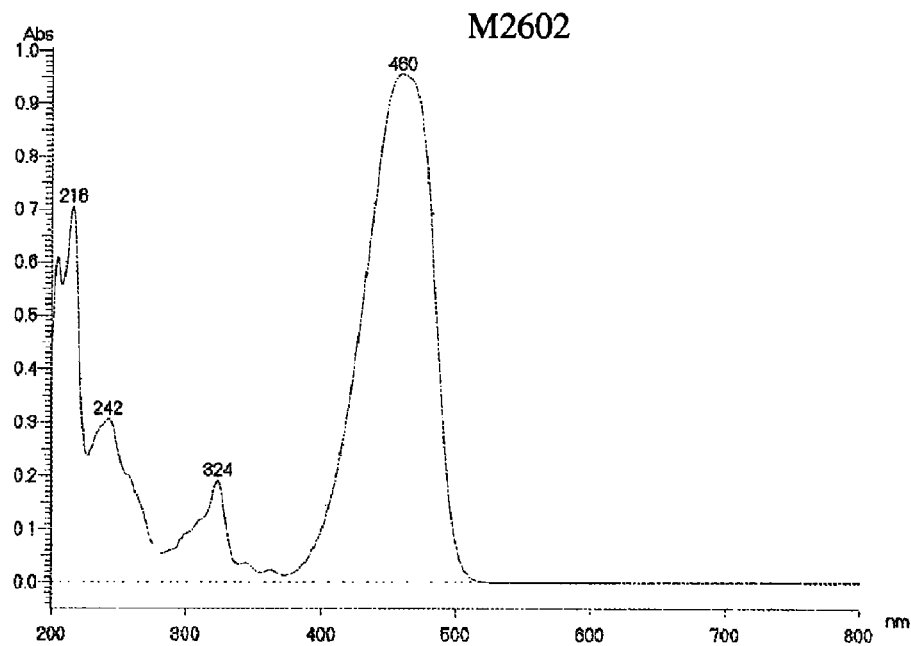
FIG. 5 is a UV-Vis absorption spectrum of the merocyanine compound M2602.

Follow the preparation procedure 3, except that the yellow crystalline powder produced as the intermediate compound in the preparation procedure 2 is replaced by the yellow crystalline powder produced as the intermediate compound in the preparation procedure 8 and another reactant, 3-methyl-1-phenyl-2-pyrazole-5-one, is replaced by the white crystalline powder produced as the intermediate compound in the preparation procedure 10. The reactant, the yellow crystalline powder prepared in the preparation procedure 8 and another reactant, the white crystalline powder prepared in the preparation procedure 10 were dissolved in DMF at room temperature to form a reaction solution. Then, the other reactant, triethylamine was added dropwise into the reaction solution, and stirred at room temperature sufficiently. Methanol was added into the reaction solution. The precipitates were filtered and washed with methanol, and dried in oven at 80° C. to give yellow powder as the final product, i.e. the merocyanine compound M2602 of the formula (5). As shown in the absorption spectrum of FIG. 5, the absorption peak ($\lambda_{max}$) of this merocyanine compound M2602 in methanol is 460 nm.

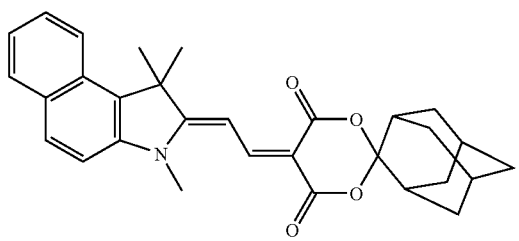

(5)

The merocyanine compound of formula (5) was dissolved in 2,2,3,3-tetrafluoropropanol. The resulting solution was filtered through the Teflon filter having a pore width of 0.2 micrometer and was applied to a polycarbonate disc by the spin-coating process. The disc with the merocyanine dye layer was tested by means of a writing test apparatus comprising a blue laser diode. The results show that the reflectivity, the writing power, the 2TCNR value of the reproduced signal satisfy the requirement profile as dye component of optical disc particularly well.

Example 5

Preparation Procedure 12

Follow the preparation procedure 1, except that 2-methyl-benzo[d]oxazole used as a reactant is replaced by 7-bromo-2,3,3-trimethyl-3H-benzo[e]indole and methyl iodide used as another reactant is replaced by butyl iodide. The reactant, 7-bromo-2,3,3-trimethyl-3H-benzo[e]indole and another reactant, butyl iodide were dissolved in acetonitrile, and heated to reflux sufficiently. After the reaction solution is cooled to 50° C., acetone is added into the reaction solution to precipitate the crude products. After cooling the room temperature, the precipitates were filtered and washed with acetone. The precipitates were dried in oven at 80° C. to give white crystalline powder as an intermediate compound.

Preparation Procedure 13

Follow the preparation procedure 2, except that the white crystalline powder produced as the intermediate compound in the preparation procedure 1 is replaced by the white crystalline powder produced as the intermediate compound in the preparation procedure 12. The reactant, white crystalline powder prepared in preparation producer 12, another reactant, N,N-diphenylformamidine, and the other reactant, sodium acetate were dissolved in ethanol, and heated to reflux sufficiently to form a reaction solution. The reaction solution were dried in oven at 80° C., and then further purified by column with ethyl acetate, to give yellow crystalline powder as an intermediate compound.

Preparation Procedure 14

Figure 6:
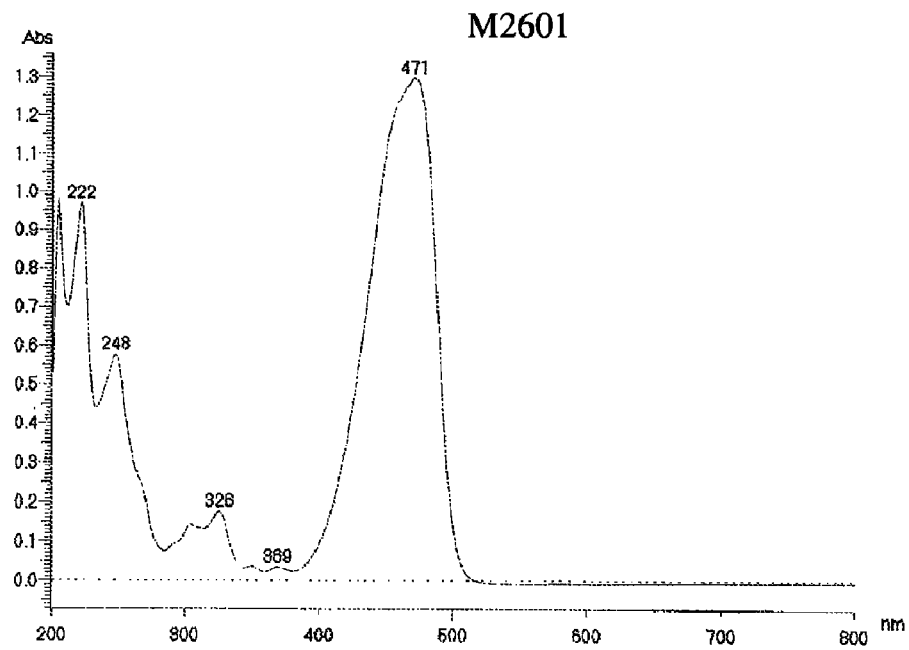
FIG. 6 is a UV-Vis absorption spectrum of the merocyanine compound M2601.

Follow the preparation procedure 3, except that the yellow crystalline powder produced as the intermediate compound in the preparation procedure 2 is replaced by the yellow crystalline powder produced as the intermediate compound in the preparation procedure 13 and another reactant, 3-methyl-1-phenyl-2-pyrazole-5-one, is replaced by the white crystalline powder produced as the intermediate compound in the preparation procedure 10. The reactant, the yellow crystalline powder prepared in preparation procedure 13 and another reactant, the white crystalline powder prepared in the preparation procedure 10 were dissolved in DMF at room temperature to form a reaction solution. Then, the other reactant, triethylamine was added dropwise into the reaction solution, and stirred at room temperature sufficiently. Methanol was added into the reaction solution. The precipitates were filtered and washed with methanol, and dried in oven at 80° C. to give yellow powder as the final product, i.e. the merocyanine compound M2601 of the formula (6). As shown in the absorption spectrum of FIG. 6, the absorption peak ($\lambda$max) of this merocyanine compound M2601 in methanol is 471 nm.

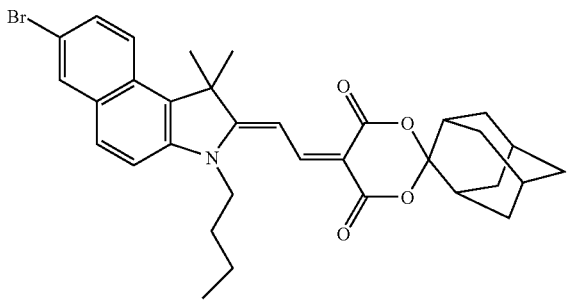

(6)

The merocyanine compound of formula (6) was dissolved in 2,2,3,3-tetrafluoropropanol. The resulting solution was filtered through the Teflon filter having a pore width of 0.2 micrometer and was applied to a polycarbonate disc by the spin-coating process. The disc with the merocyanine dye layer was tested by means of a writing test apparatus comprising a blue laser diode. The results show that the reflectivity, the writing power, the 2TCNR value of the reproduced signal satisfy the requirement profile as dye component of optical disc particularly well.

Example 6

Preparation Procedure 15

Follow the preparation procedure 1, except that 2-methylbenzo[d]oxazole used as a reactant is replaced by 2-methylquinoline and methyl iodide used as another reactant is replaced by butyl iodide. The reactant, 2-methylquinoline and another reactant, butyl iodide were dissolved in acetonitrile, and heated to reflux sufficiently to form a reaction solution. After the reaction solution is cooled to 50° C., acetone is added into the reaction solution to precipitate the crude products. After cooling to room temperature, the precipitates were filtered and washed with acetone. The precipitates were dried in oven at 80° C. to give white crystalline powder as an intermediate compound.

Preparation Procedure 16

Follow the preparation procedure 2, except that the white crystalline powder produced as the intermediate compound in the preparation procedure 1 is replaced by the white crystalline powder produced as the intermediate compound in the preparation procedure 15. The reactant, the white crystalline powder prepared in preparation procedure 15, another reactant, N,N-diphenylformamidine, and the other reactant, sodium acetate were dissolved in tethanol, and heated to reflux sufficiently to form a reaction solution. The reaction solution were dried in oven at 80° C., and then further purified by column with ethyl acetate, to give brown crystalline powder as an intermediate compound.

Preparation Procedure 17

Figure 7:
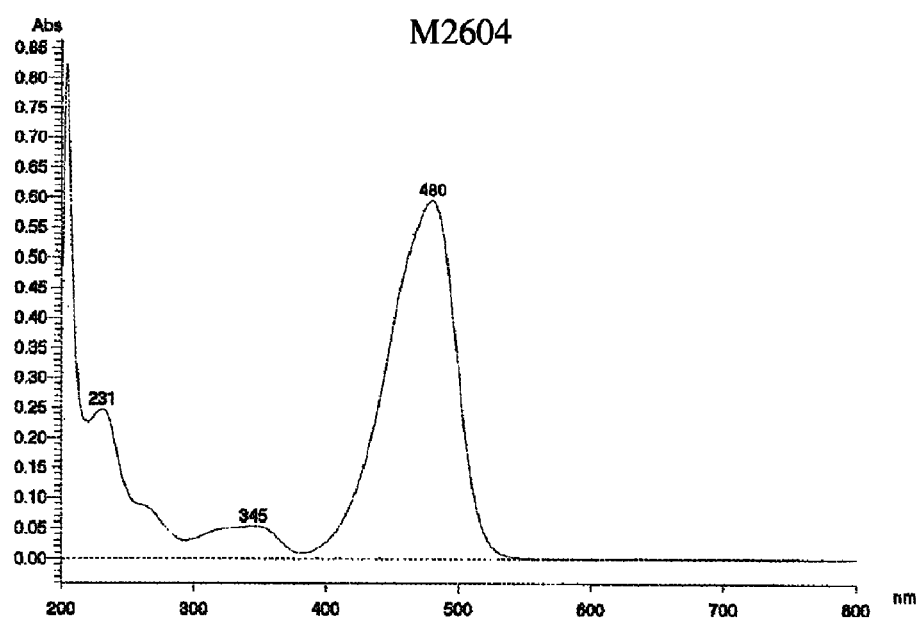
FIG. 7 is a UV-Vis absorption spectrum of the merocyanine compound M2604.

Follow the preparation procedure 3, except that the yellow crystalline powder produced as the intermediate compound in the preparation procedure 2 is replaced by the brown crystalline powder produced as the intermediate compound in the preparation procedure 16 and another reactant, 3-methyl-1-phenyl-2-pyrazole-5-one, is replaced by the white crystalline powder produced as the intermediate compound in the preparation procedure 10. The reactant, the yellow crystalline powder prepared in preparation procedure 16 and another reactant, the white crystalline powder prepared in the preparation procedure 10 were dissolved in DMF at room temperature to form a reaction solution. Then, the number of triethylamine was added dropwise into the reaction solution, and stirred at room temperature sufficiently. Methanol was added into the reaction solution. The precipitates were filtered and washed with the methanol, and dried in oven at 80° C. to give orange powder as the final product, i.e. the merocyanine compound M2604 of the formula (7). As shown in the absorption spectrum of FIG. 7, the absorption peak (λmax) of this merocyanine compound M2604 in methanol is 480 nm.

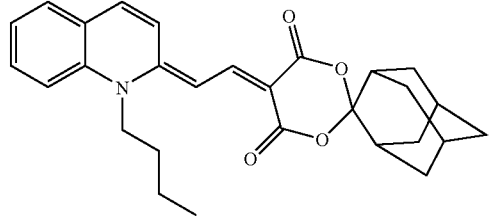

(7)

The merocyanine compound of formula (7) was dissolved in 2,2,3,3-tetrafluoropropanol The resulting solution was filtered through the Teflon filter having a pore width of 0.2 micrometer and was applied to a polycarbonate disc by the spin-coating process. The disc with the merocyanine dye layer was tested by means of a writing test apparatus comprising a blue laser diode. The results show that the reflectivity, the writing power, the 2TCNR value of the reproduced signal satisfy the requirement profile as dye component of optical disc particularly well.

Preparation Procedure 18

Figure 8:
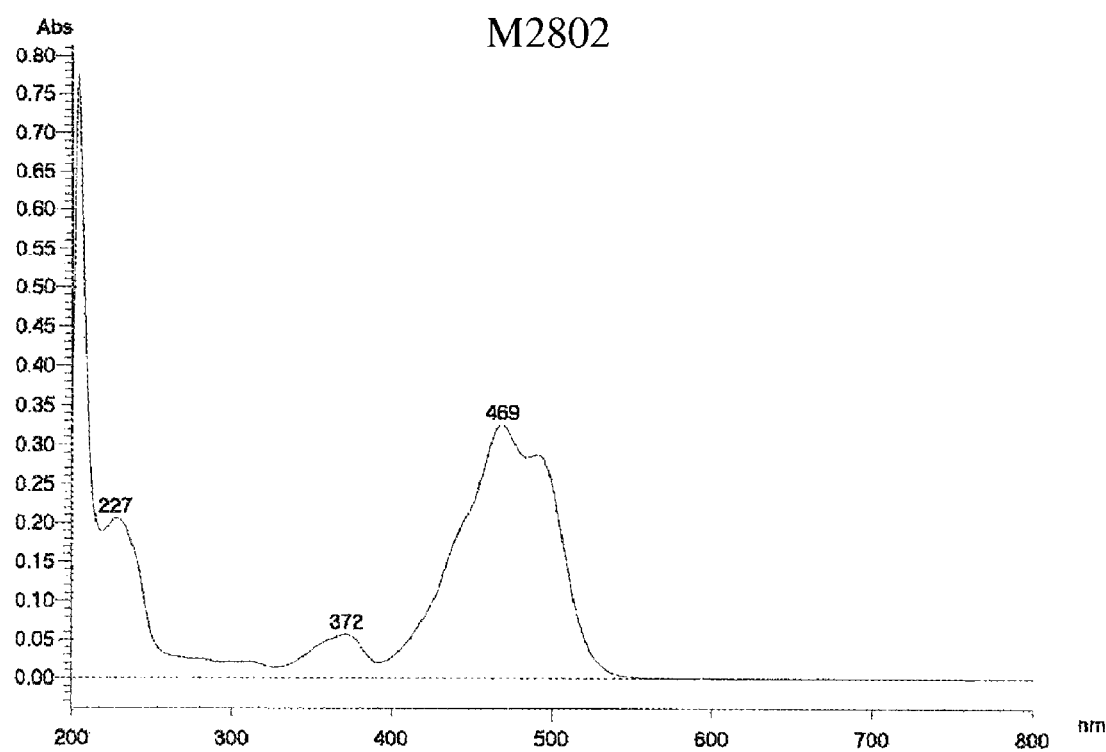
FIG. 8 is a UV-Vis absorption spectrum of the merocyanine compound M2802.

Follow the preparation procedure 3, except that the yellow crystalline powder produced as the intermediate compound in the preparation procedure 2 is replaced by the brown crystalline powder produced as the intermediate compound in the preparation procedure 16 and the reactant, 3-methyl-1-phenyl-2-pyrazole-5-one, is replaced by ethyl-2-cyanoacetate. The reactant, the yellow crystalline powder prepared in the preparation procedure 16 and another reactant, ethyl-2-cyanoacetate were dissolved in DMF at room temperature to form a reaction solution. Then, the number of triethylamine was added dropwise into the reaction solution, and stirred at room temperature sufficiently. Methanol was added into the reaction solution. The precipitates were filtered and washed with methanol, and dried in oven at 80° C. to give orange powder as the final product, i.e. the merocyanine compound M2802 of the formula (8). As shown in the absorption spectrum of FIG. 8, the absorption peak (λmax) of this merocyanine compound M2802 in methanol is 469 nm.

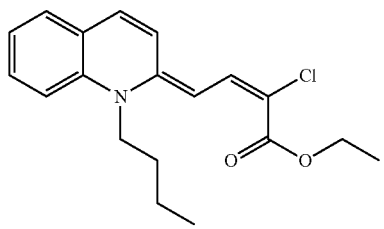

(8)

The merocyanine compound of formula (8) was dissolved in 2,2,3,3-tetrafluoropropanol. The resulting solution was filtered through the Teflon filter having a pore width of 0.2 micrometer and was applied to a polycarbonate disc by the spin-coating process. The disc with the merocyanine dye layer was tested by means of a writing test apparatus comprising a blue laser diode. The results show that the reflectivity, the writing power, the 2TCNR value of the reproduced signal satisfy the requirement profile as dye component of optical disc particularly well.

Moreover, after the merocyanine compound of the general formula (1) is dissolved in suitable solvents and applied to a carrier, the carrier with the merocyanine dye can be used to absorb blue laser light in organic photo conductor, laser optical data carrier or organic light-emitting diodes. By modification of functional groups, this dye component has improved properties such as photosensitivity, solubility, light fastness and the optical disc containing this dye component may be written in a reduced writing power.

While the invention has been described in terms of what is presently considered to be the most practical and preferred embodiments, it is to be understood that the invention needs not to be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A blue laser light-absorbent substance comprising a merocyanine compound, wherein the merocyanine compound has a structural formula selected from:

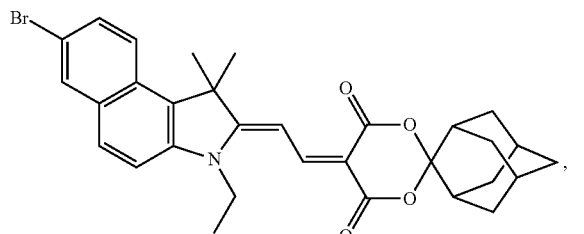

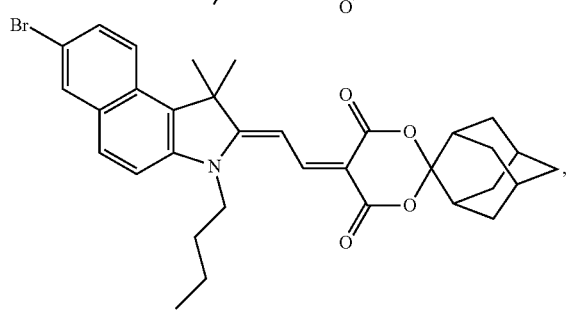

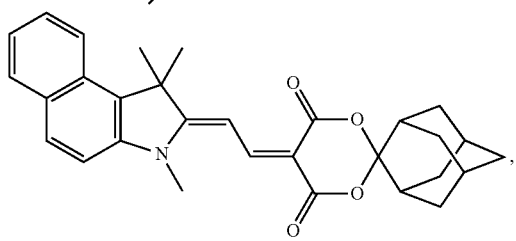

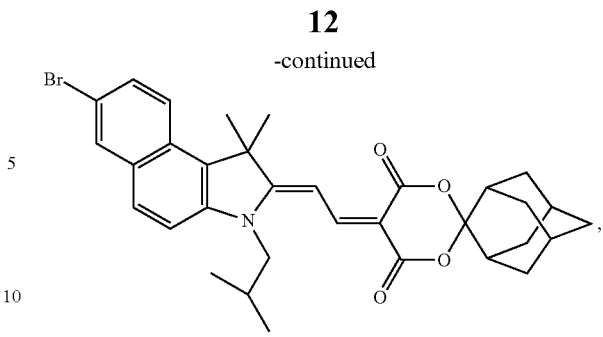

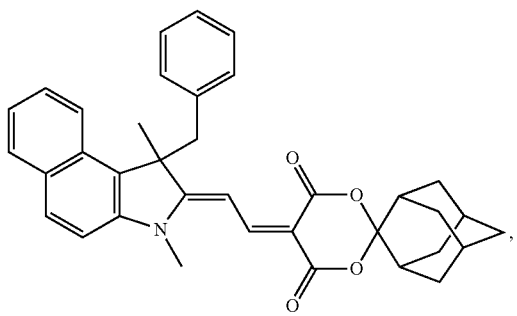

and

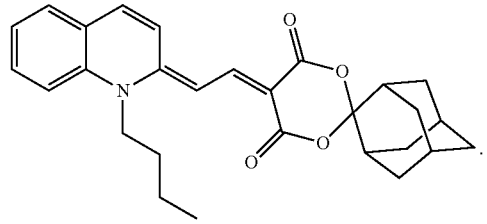

2. The blue laser light-absorbent substance according to claim 1, wherein the merocyanine compound has an absorption peak in the spectral range of from 390 to 490 nm.

3. The blue laser light-absorbent substance according to claim 1, wherein the indole aromatic group is bromide-substituted.

4. The blue laser light-absorbent substance according to claim 1, wherein the 5-membered azacyclic ring of the indole aromatic group is benzyl-substituted.

* * * * *